United States Patent [19]

Chalk

[11] 4,096,169

[45] Jun. 20, 1978

[54] AROMATIC CARBONATES

[75] Inventor: Alan J. Chalk, Kinnelon, N.J.

[73] Assignee: General Electric Company, Schenectady, N.Y.

[21] Appl. No.: 731,496

[22] Filed: Oct. 12, 1976

[51] Int. Cl.$^2$ .............................................. C07C 68/00
[52] U.S. Cl. ............................... 260/463; 260/47 XA
[58] Field of Search .......................... 260/463, 47 XA

[56] References Cited

U.S. PATENT DOCUMENTS

| | | | |
|---|---|---|---|
| 3,114,762 | 12/1963 | Mador et al. | 260/463 |
| 3,846,468 | 11/1974 | Perrotti et al. | 260/463 |

OTHER PUBLICATIONS

P. P. Borisov, Chem. Abstracts, 32:2414, Apr.–Jun. 1938.

*Primary Examiner*—Elbert L. Roberts
*Assistant Examiner*—Molly C. Eakin
*Attorney, Agent, or Firm*—F. W. Turner; J. T. Cohen; M. Snyder

[57] ABSTRACT

An aromatic carbonate process comprising contacting a phenol, carbon monoxide in the presence of a base, Group VIIIB element selected from ruthenium, rhodium, palladium, osmium, iridium or platinum having an oxidation state greater than zero. The resulting aromatic mono- and polycarbonates are useful in the preparation of polycarbonates or as polycarbonates, per se, respectively, which can be molded or formed into films, sheets, fibers, laminates or reinforced plastics by conventional techniques.

22 Claims, No Drawings

AROMATIC CARBONATES

CROSS-REFERENCE TO RELATED APPLICATIONS

An aromatic carbonate process cross-referenced to related applications. This invention is related to my copending U.S. Pat. application Ser. No. 731,495, filed concurrently herewith and J. E. Hallgren, U.S. patent application Ser. Nos. 731,443; 731,494; and 731,493; filed concurrently herewith. All of the aforesaid applications are assigned to the same assignee as the assignee of this application.

BACKGROUND OF THE INVENTION

1. Field of the Invention

This invention relates to an aromatic carbonate process comprising contacting a phenol, carbon monoxide in the presence of a base, a Group VIIIB element selected from ruthenium, rhodium, palladium, osmium, iridium or platinum having an oxidation state greater than zero to form a reaction mixture. The aromatic carbonate can be isolated or separated from the reaction mixture.

2. Description of the Prior Art

Mador et al, in U.S. Pat. No. 3,114,762, issued Dec. 17, 1963, describes the preparation of aliphatic carbonates by the reaction of aliphatic alcohols with carbon monoxide carried out in the presence of a salt of palladium or platinum metal.

Perrotti et al., in U.S. Pat. No. 3,846,468, issued Nov. 5, 1974, describes the preparation of carbonic acid esters by the reaction of an aliphatic and aromatic alcohol with carbon monoxide and oxygen carried out in the presence of copper complexed with an organic molecule. Although the disclosure of Perrotti et al. suggests that elements such as iron, cobalt and nickel are effective catalysts for the reaction of alcohols with carbon monoxide in the presence of oxygen, it was found that when iron, cobalt or nickel compounds are substituted for the Group VIIIB elements employed in my process for making aromatic carbonates, such carbonates could not be obtained under these conditions.

DESCRIPTION OF THE INVENTION

This invention embodies an aromatic carbonate process comprising contacting a phenol with carbon monoxide in the presence of a base, and a Group VIIIB element selected from ruthenium, rhodium, palladium, osmium, iridium or platinum having an oxidation state greater than zero.

The reactants and the resulting reaction products of my process can be illustrated by the following general equations which are furnished for illustrative purposes only since the reaction mechanisms involved in the preparation of aromatic monocarbonates (Eq. 1) and polycarbonates (Eq. 2) may be much more complex:

$$PdCl_2 + 2R'OH + 2R_3N + CO \rightarrow Pd° + R'_2CO_3 + 2R_3{}^+NH\ Cl^-$$
Eq. 1 or

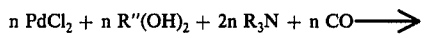
Eq. 2

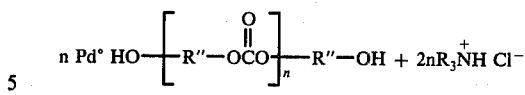

wherein R is an alkyl radical (including cycloalkyl), R' is an aryl radical, R'' is an arene radical, and $n$ is a number equal to at least 1.

Any nuclearly hydroxy substituted aromatic compound can be used in my process and is defined herein and in the appended claims as "a phenol". Illustratively the phenol or phenolic reactant can be described by the formula:

$$R_a\text{-}(OH)_x,\qquad \text{I.}$$

wherein $R_a$ represents an aromatic radical wherein the —OH radical is attached directly to an aromatic ring carbon atom and $x$ is a number being at least equal to 1, advantageously from 1 to 4 and preferably from 1 to 2. The $R_a$ radical can be carbo- or heteromonocyclic, polycyclic, or fused polycyclic, and can have two or more cyclic systems (monocyclic, polycyclic or fused polycyclic systems) which are connected to each other by single or double valence bonds, or bi- or multivalent radicals.

Preferred phenolic reactants are phenols containing from 6 to 30, and more preferably from 6 to 15 carbon atoms. Illustrative of commercially important phenolic reactants included within the above description are the following: phenol itself (hydroxy benzene), naphthol, ortho-, meta-, or paracresol, catechol, cumenol, xylenol, resorcinol, the various isomers of dihydroxy diphenyl, the various isomers of dihydroxynaphthalene, bis(4-hydroxyphenyl)propane-2,2,α,α'-bis(4-hydroxyphenyl)-p-diisopropylenebenzene, 4,4'-dihydroxy-3,5,3',5'-tetrachlorophenylpropane-2,2, 4,4'-dihydroxy-3,5,3',5'-tetrachloro-phenylpropane-2,2 and 4,4'-dihydroxy-3,5,3',5'-tetrabromo-phenylpropane-2,2, phloroglucinol, dihydroxy oligomers, for example an oligomer derived from bisphenol-A, etc.

A general preferred bisphenol that can be used in my process can be described by the following formula:

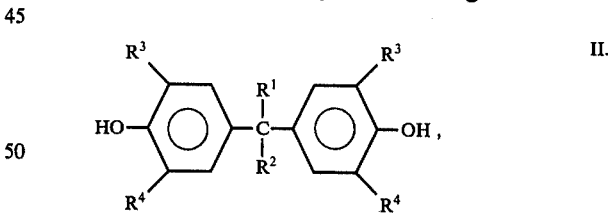

where $R^1$ and $R^2$ are hydrogen, $C_{1-4}$ alkyl or phenyl, at least one of $R^3$ is hydrogen and the other is hydrogen or $C_{1-4}$ alkyl, and at least one of $R^4$ is hydrogen and the other is hydrogen or $C_{1-4}$ alkyl.

Especially preferred is bis(4-hydroxyphenyl)propane-2,2, also commonly known as "bisphenol-A" (BPA).

Any Group VIIIB element, defined herein and in the appended claims as "a Group VIIIB element", can be employed subject to the proviso that it is selected from ruthenium, rhodium, palladium, osmium, iridium or platinum and has an oxidation state greater than zero.

In one embodiment of the invention, the oxidation state of the element is at least +2. The Group VIIIB elements can be present in ionic, inorganic or organic compound or complex, etc. forms. The Group VIIIB elements can be employed in oxide, halide, nitrate, sulfate, oxalate, acetate, carbonate, propionate, hydroxide, tartrate, etc., forms.

Group VIIIB elements in complex form, e.g., with ligands, such as carbon monoxide, nitriles, tertiary amines, phosphines, arsines, or stibines, etc., can be employed and illustratively are often represented by those skilled in the art as mono-, di-, or polynuclear Group VIIIB element forms. Generally, the dimeric or polymeric forms are considered to contain Group VIIIB atoms bridged by ligands, halogens, etc. Preferred Group VIIIB elements form homogeneous mixtures when combined with the phenolic reactants, especially when the process is carried out under liquid phase reaction conditions.

Illustrative of generally preferred Group VIIIB element compounds or complexes that can be used in my process follow: $RuCl_2$, $RuBr_2$, $RuI_2$, $Ru(CO)_2Cl_2$, $Ru(CO)_2I_2$, $Ru(CO)_4Cl_2$, $Ru(CO)_4Br_2$, $Ru(CO)_4I_2$, $RuCl_3$, $RuBr_3$, $RuI_3$, etc., $PdCl_2$, $PdBr_2$, $PdI_2$, $[Pd(CO)Cl_2]_2$, $[Pd(CO)Br_2]_2$, $[Pd(CO)I_2]_2$, $(C_6H_5CN)_2PdCl_2$, $PdCl_4$, $Pd(OH)_2\text{—}(CNC_4H_9)_2$, $PdI_2(CNC_6H_5)_2$, $Pd(OH)_2(CNCH_3OC_6H_5)_2$, $Pd(CNC_4H_9)_4$, etc., $Rh(CO)Cl_2$, $Rh(CO)Br_2$, $Rh(CO)I_2$, $Rh_2Cl_2(CO)_2$, $Rh_2(CO)_4Cl_2$, $Rh_2(CO)_4Br_2$, $Rh_2(CO)_4I_2$, $[Rh(CO)_2Cl]_2$, $RhCl_3$, $RhBr_3$, $RhI_3$, etc., $Os(CO)_3Cl_2$, $Os(CO)_3Br_2$, $Os(CO)_3I_2$, $Os(CO)_4Cl_2$, $Os(CO)_4Br_2$, $Os(CO)_4I_2$, $Os(CO)_8Cl_2$, $Os(CO)_8Br_2$, $Os(CO)_8I_2$, $OsCl_2$, $OsCl_3$, $OsI_2$, $OsI_3$, $OsBr_3$, $OsBr_4$ and $OsCl_4$, etc., $IrCl_3$, $IrCl_3(CO)$, $Ir_2(CO)_8$, $IrCl_3$, $IrBr_3$, $IrCl_3$, $IrBr_4$, $IrI_4$, etc., $PtCl_2$, $PtBr_2$, $PtI_2$, $Pt(CO)_2Cl_2$, $Pt(CO)_2Br_2$, $Pt(CO)_2I_2$, $Pt(CO)_2Cl_4$, $Pt(CO)_2Br_4$, $Pt(CO)_2I_4$, $Pt(CO)_3Cl_4$, $Pt(CO)_3Br_4$, $Pt(CO)_3I_4$, $PtCl_2(CNC_6H_5)_2$, etc.

Illustrative of ligands that can be associated with the Group VIIIB elements in complex form — other than and, optionally, in addition to carbon monoxide — include organic tertiary amines, phosphines, arsines and stibine ligands of the following formula:

$(E)_3Q$, wherein, independently, each E is selected from the radicals Z and OZ, where independently each Z is selected from organic radicals containing from 1 to 20 carbon atoms, and wherein independently each Q is selected from nitrogen, phosphorus, arsenic or antimony. Preferably, the organic radicals are free of active hydrogen atoms, reactive unsaturation, and are oxidatively stable. More preferably, the E groups are alkyl, cycloalkyl and aryl hydrocarbyl radicals and mixtures thereof, such as alkaryl, aralkyl, alkcycloalkyl containing from 1 to 10 carbon atoms, and even more preferably each E is an aryl group containing from 6 to 10 carbon atoms.

Illustrative of generally known presently preferred Group VIIIB complexes which contain ligands include the following: $RuCl_2[P(C_6H_5)_3]_4$, $[Rh(CO)_2Cl]_2$, $trans[(C_2H_5)_3P]_2$, $[P(C_4H_9)_3]_2PdCl_4$, $[(C_6H_5)_3P]_3IrCl_3\cdot(CO)$, $[(C_6H_5)_3As]_3IrCl_3(CO)$, $[(C_6H_5)_3Sb]_3IrCl_3(CO)$, $[(C_6H_5)_3P]_2PtCl_2$, $[(C_6H_5)_3P]_2PtF_2$, $[(C_6H_5)_3P]_2PtF_2(CO)_2$, $Pt[(C_6H_5)_3P]_2(CO)_2$, etc.

The Group VIIIB element compounds and/or complexes can be prepared by any method well-known to those skilled in the art including the methods referenced in the following publications:

*Reactions of Transition-Metal Complexes*, J. P. Candlin, K. A. Taylor and D. T. Thompson, Elsevier Publishing Co. (1968) Library of Congress Catalog Card No. 67-19855;

*Organic Syntheses Via Metal Carbonyls*, Vol. 1, I. Wender and P. Pinto, Interscience Publishers (1968) Library of Congress Catalog Card No. 67-13965;

*The Organic Chemistry of Palladium*, Vols. I and II, P. M. Maitlis, Acedemic Press (1971) Library of Congress Catalog Card No. 77-162937;

*The Chemistry of Platinum and Palladium*, F. R. Hartley, Halsted Press (1973);

as well as those described in U.S. and foreign technical journals and patents.

The process can be carried out in the absence of any solvent, e.g. where the phenolic reactant acts as both a reactant and a solvent, however preferably is carried out in the presence of a solvent, and more preferably solvents of the general class: methylene chloride, ethylene dichloride, chloroform, carbontetrachloride, tetrachloroethylene, nitromethane, hexane, 3-methylpentane, heptane, cyclohexane, methylcyclohexane, cyclohexane, isooctane, p-cymene, cumene, decalin, toluene, benzene, diphenylether, dioxane, thiophene, dimethylsulfide, ethylacetate, tetrahydrofuran, chlorobenzene, anisol, bromobenzene, o-dichlorobenzene, methylformate, iodobenzene, acetone, acetophenone, etc., and mixtures thereof.

In general, the process can be carried out in any basic reaction medium, preferably, that provided by the presence of any inorganic or organic base which will dissolve the phenolic reactant. Representative of basic species which can be employed are the following: elemental alkali and alkaline earth methals; basic quarternary ammonium, quarternary phosphonium or tertiary sulfonium compounds; alkali or alkaline earth metal hydroxides; salts of strong bases and weak organic acids; primary, secondary or tertiary amines; etc. Specific examples of the aforementioned are sodium, potassium, magnesium metals, etc.; quarternay ammonium hydroxide, tetraethyl phosphonium hydroxide, etc.; sodium, potassium, lithium, and calcium hydroxide; quaternary phosphonium, tertiary sulfonium, sodium, lithium and barium carbonate, sodium acetate, sodium benzoate, sodium methylate, sodium thiosulfate sodium compounds, e.g., suflfide, tetrafulfide, cyanide, hydride and borohydride potassium fluoride, methylamine, isopropylamine, methylethylamine, allylethylamine, ditert-butylamine, dicyclohexylamine, dibenzylamine, tert-butylamine, allyldiethylamine, benzyldimethylamine, diactylchlorobenzylamine, dimethylphenethylamine, 1-dimethylamino-2-phenylpropane, propanediamine, ethylenediamine, N-methylethylenediamine, N,N'-dimethylethylenediamine, N,N,N'-tritert-butylpropanediamine, N,N',N',N''-tetramethyldiethylenetriamine, pyridine, aminomethylpyridines, pyrrole, pyrrolidine, piperidine, 2,2,6,6-N-pentamethylpiperidine, imidazole, etc. Especially preferred bases are sterically hindered amines, e.g. diisopropylmonoethylamine, 2,2,6,6,N-pentamethylpiperidine, etc.

Any amount of base can be employed. In general, effective mole ratios of base to Group VIIIB elements are within the range of from about 0.000001:1 to about 100:1 or higher, preferably from 0.5:1 to about 10:1, and more preferably from 1:1 to 2:1. Generally, mole ratios of at least 1:1 enhances both the reaction rate and the yield of aromatic carbonate.

Any amount of Group VIIIB element can be employed. For example, Group VIIB element to phenol mole proportions within the range of from about 0.001:1 or lower to about 1000:1 or higher are effective, however, preferably ratios of from 0.1:1 to 10:1, and more preferably at least 1:1 are employed in order to insure that optimum conversion of the phenol to aromatic carbonate occurs.

Any amount of carbon monoxide can be employed. Preferably the process is carried out under positive carbon monoxide pressure, e.e., where carbon monoxide is present in stoichiometric amounts sufficient to form the desired aromatic mono- or poly-carbonate. In general, carbon monoxide pressures within the range of from about ½ to about 500 atmospheres, or even higher, can be employed with good results. Presently preferred are CO pressures within the range of from 1 to 200 atmospheres.

Any reaction temperature can be employed. In general, optimum reaction temperatures are 0° C. or even lower to 200° C. or even higher and more often 0° C. to 50° C.

Any reaction time period can be employed. Generally optimum reaction time periods are about 0.1 hour or even less to about 10 hours or even more.

Any amount of solvent, preferably inert, can be employed. In general, optimum solvent to phenolic reactant mole proportions are from 0.5:99.5 to 99.5:0.5, preferably from 50:50 to 99:1.

Following some of the procedures described herein, aromatic salicylates can be formed. These aromatic salicylates, i.e. aromatic compounds which can be defined as "salicylate" can be generically described by the following formula:

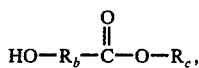

wherein $R_b$ represents an aromatic radical with the hydroxyl radical positioned ortho relative to the carboxylate, i.e.

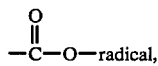

and $R_c$ represents an aromatic radical. The $R_b$ and $R_c$ radicals can be carbo- or hetero-monocyclic, polycyclic, or fused polycyclic, and can have two or more cyclic systems (monocyclic, polycyclic or fused polycyclic systems) which are directly joined to each other by single or double valence bonds, or by bi- or multivalent radicals. The separation and recovery of the salicylates inherent in the practice of my invention is described in the U.S. patent application Ser. No. 731,443 of J. E. Hallgren, filed concurrently herewith.

In order that those skilled in the art may better understand my invention, the following examples are given which are illustrative of the best mode of this invention, however, these examples are not intended to limit the invention in any manner whatsoever. In the examples, unless otherwise specified all parts are by weight and the reaction products were verified by infrared spectrum, C-13 nuclear magnetic resonance and mass spectrometry.

EXAMPLE I

Preparation of diphenyclarbonate using hydroxybenzene, carbon monoxide, diisopropylmonoethylamine, and bis(benzonitrile)palladium(II) dichloride.

0.26 g. bis(benzonitrile)palladium(II) dichloride, e.g. PdCl₂(PhCN)₂ was dissolved in 7 ml. benzene and 0.9 g. of phenol was added. To this solution 0.5 ml. of diisopropylmonoethylamine was added whereby a dark red solution resulted. Carbon monoxide was bubbled through the resulting solution until no further palladium precipitated. The resulting benzene solution was diluted to approximately 20 ml. and then extracted with excess dilute (20 ml. 2N) hydrochloric acid three times, then with dilute (20 ml. 2N) sodium hydroxide three times. The resulting benzene solution was then evaporated to dryness and the mixture recrystallized from heptane to yield off-white crystals of diphenylcarbonate identified by infrared spectrum, mass spectrum, C-13 nmr, and melting point.

EXAMPLE II

Preparation of diphenylcarbonate using hydroxybenzene, carbon monoxide, diisopropylmonoethylamine and bis(benzonitrile)palladium(II) dichloride.

Carbon monoxide was bubbled through a mixture containing 0.26 g. of bis(benzonitrile)palladium(II) dichloride, 0.9 g. of phenol, and 7 ml. of benzene, and 0.5 ml. of diisopropylmonoethylamine. The solution immediately turned black and palladium metal precipitated. After 20 minutes, the carbon monoxide was stripped and the reaction mixture was centrifuged. A sample of the resulting supernatant liquid was decanted and the benzene was evaporated. The decanted sample was analyzed by ir and the presence of diphenylcarbonate was confirmed by mass spectrometry data.

EXAMPLE III

Preparation of diphenylcarbonate using hydroxybenzene carbon monoxide, diisopropylmonoethylamine and bis(benzonitrile)palladium(II) dichloride.

A reaction vessel was charged with 1.50 g. (4.0 mml.) of bis(benzonitrile)palladium(II) dichloride, 0.77 g. (8.0 mmol.) of phenol, and 10 ml. of methylene chloride. The mixture was stirred, flushed slowly with carbon monoxide, and 1.5 g. (11.6 mmol.) of diisopropylmonoethylamine was added. The solution immediately turned black and palladium metal precipitated. After stirring at room temperature for three hours, the mixture was filtered. The precipitate was washed with methylene chloride, then dried in a stream of air, to yield 0.43 g. (10%) of palladium metal. The filtrate was analyzed and the presence of 0.23 g. (52% yield) of diphenyl carbonate and 0.45 g. (53%) of phenyl salicylate of the formulas, respectively, was formed:

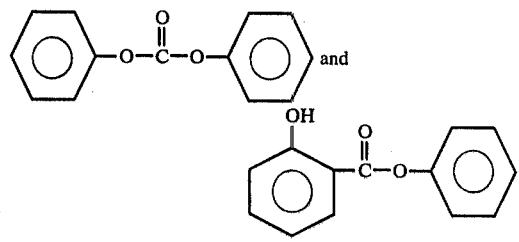

EXAMPLE IV

Preparation of 4,4'-dimethyldiphenylcarbonate using 4-methylphenol as the phenolic reactant.

A reaction vessel was charged with 0.77 g. (2.0 mmol.) of bis(benzonitrile)palladium(II) dichloride, 7 ml. of methylene chloride, and a solution of 0.22 g. (2.0 mmol.) of 4-methylphenol plus 0.52 g. (4.0 mmol.) of diisopropylmonoethylamine dissolved in 5 ml. of methylene chloride. Carbon monoxide was bubbled through the solution for two hours. The analysis of the products was 0.15 g. (60%) of 4,4'-dimethyldiphenyl carbonate and 0.18 g. (38%) of 4'-methylphenyl-2-hydroxy-5-methyl benzoate of the formulas, respectively:

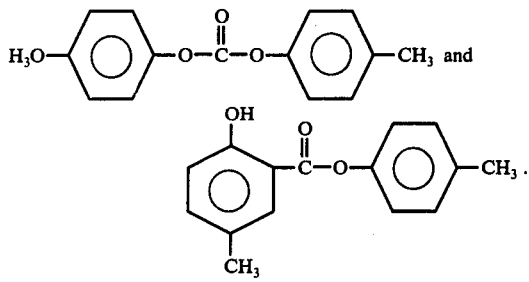

EXAMPLE V

Preparation of 4,4'-(α,α-dimethylbenzyl)diphenyl carbonate using p-cumyl phenol as the phenolic reactant.

A reaction vessel was charged with 0.77 g. (2.0 mmol.) of bis(benzonitrile)palladium(II) dichloride, 7 ml. of methylene chloride, and a solution of 0.42 g. (2.0 mmol.) of p-cumylphenol plus 0.52 g. (4.0 mmol.) of diisopropylmonoethylamine dissolved in 7 ml. of methylene chloride. The mixture was stirred to effect solution and carbon monoxide bubbled through the solution overnight. Subsequent work-up showed the presence of 0.32 g. (71% yield) of 4,4'-(α,α-dimethylbenzyl)diphenyl carbonate and 0.18 g. (20%) of 4-(α,α-dimethylbenzyl)phenyl 5-(α,α-dimethylbenzyl)-2-hydroxybenzoate of the formulas, respectively:

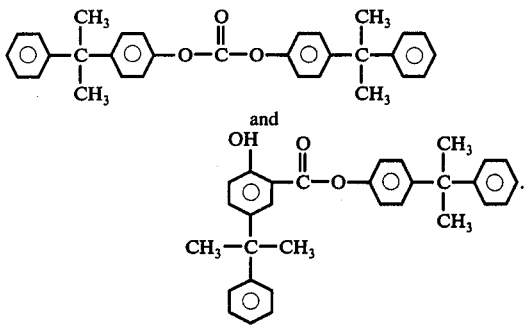

EXAMPLE VI

Preparation of 4,4'-dichlorodiphenyl carbonate using 4-chlorophenol as the phenolic reactant.

A reaction vessel was charged with 0.26 g. (2.0 mmol.) of 4-chlorophenol, 0.77 g. (2.0 mmol.) of bis(-benzonitrile)palladium(II) dichloride and 7 ml. of methylene chloride. To this was added 0.52 g. (4.0 mmol.) of diisopropylmonoethylamine and carbon monoxide was bubbled through the solution. Precipitation of palladium metal was quite slow and the reaction was continued overnight. Subsequent work-up and analysis showed the presence of 0.19 g. (67% yield) of 4,4'-dichlorodiphenyl carbonate of the formula:

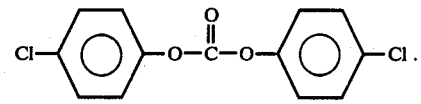

EXAMPLE VII

Preparation of 4,4'-dimethyldiphenylcarbonate under pressure.

The reaction medium contained 4.03 g. (1.05 mmol.) of bis(benzonitrile)palladium(II) dichloride, 20 ml. of methylene chloride, 0.108 g. of 4-methylphenol, 0.131 g. of diisopropylmonoethylamine, and sufficient carbon monoxide to charge the vessel to 65 psi. The product yield was 38% of 4,4'-dimethyldiphenyl carbonate and 41% of 4'-methylphenyl-2-hydroxy-5-methyl benzoate.

EXAMPLE VIII

Preparation of 4,4'-dimethyldiphenylcarbonate using palladium(II) dichloride.

A reaction vessel was charged with 10 ml. of methylene chloride, 0.108 g. (1.0 mmol.) of 4-methylphenol, 0.137 g. (1.1 mmol.) of diisopropylmonoethylamine, and sufficient carbon monoxide to pressure the vessel to 65 psi. 0.199 g. (1.12 mmol.) of palladium(II) dichloride, i.e. PdCl$_2$, was added. The product yield was 0.98 g. (81% of 4,4'-dimethyldiphenyl carbonate and 0.08 g. (7%) of 4'-methylphenyl-2-hydroxy-5-methyl benzoate.

EXAMPLE IX

Preparation of 4,4'-dimethyldiphenylcarbonate using pyridine as the base.

The reaction vessel contained 0.180 g. (1.02 mmol.) of palladium(II) dichloride, 10 ml. of methylene chloride, 0.224 g. (2.26 mmol.) of 4-methylphenol, 0.174 g. (2.20 mmol.) of pyridine, and sufficient carbon monoxide to charge the vessel to 62 psi. The product yield was 3% of 4,4'-dimethyldiphenyl carbonate.

EXAMPLE X

Preparation of 4,4'-dimethyldiphenyl carbonate using 4-methyl sodium phenoxide as the base.

The reaction vessel contained 0.184 g. (1.04 mmol.) of palladium(II) dichloride, 10 ml. of methylene chloride, 0.125 g. (1.16 mmol.) of 4-methylphenol, 0.080 g. (0.62 mmol.) of 4-methyl sodium phenoxide and sufficient carbon monoxide to charge the vessel to 63 psi. The product yield was 5% of 4,4'-dimethyldiphenyl carbonate and 8% of 4'-methylphenyl-2-hydroxy-5-methyl benzoate.

EXAMPLE XI

Preparation of 4,4'-dimethyldiphenyl carbonate using potassium carbonate as a base.

The reaction vessel contained 0.182 g. (1.03 mmol.) of palladium(II) dichloride, 10 ml. of methylene chloride, 0.233 g. (2.16 mmol.) of 4-methylphenol, 0.320 g. (2.32 mmol.) of potassium carbonate, and sufficient carbon monoxide to charge the vessel to 64 psi. The product yield was 4% of 4,4'-dimethyldiphenyl carbonate and 1% of 4'-methylphenyl-2-hydroxy-5-methyl benzoate.

EXAMPLE XII

Preparation of 4,4'-dimethyldiphenyl carbonate using sodium carbonate as a base.

The reaction vessel contained 0.197 g. (1.11 mmol.) of palladium(II) dichloride, 10 ml. of methylene chloride, 0.238 g. (2.21 mmol.) of 4-methylphenol, 0.283 g. (2.67 mmol.) of sodium carbonate, and sufficient carbon monoxide to charge the vessel to 66 psi. The product was 2% of 4,4'-dimethyldiphenyl carbonate.

EXAMPLE XIII

Preparation of 4,4'-dimethyldiphenyl carbonate using potassium fluoride as a base.

The reaction vessel contained 0.182 g. (1.00 mmol.) of palladium(II) dichloride, 10 ml. of methylene chloride, 0.248 g. (2.3 mmol.) of 4-methylphenol, 0.150 g. (2.6 mmol.) of potassium fluoride, and sufficient carbon monoxide to charge the vessel to 65 psi. The product yield was 3% of 4,4'-dimethyldiphenyl carbonate and 1% of 4'-methylphenyl-2-hydroxy-5methyl benzoate.

EXAMPLE XIV

This procedure, which is not an example of this invention, illustrates the attempted preparation of diphenylcarbonate employing the teachings of Perrotti et al., U.S. Pat. No. 3,846,468, by contacting hydroxybenzene with carbon monoxide in the presence of di(triethylphosphine)nickel tribromide.

Di(triethylphosphine)nickel tribromide was prepared by the procedure of Jensen, Nygaard and Pedersen, Acta Chim. Scand. 17, 1126 (1963). The procedure involved the addition of 0.45 g. (2.81 ml.) of bromine which had previously been combined with 1.5 ml. of benzene to 2.5 grams (5.5 mmol.) of di(triethyl phosphine)nickel dibromide, i.e. $[(H_5C_2)_3P]_2NiBr_2$, slurried in 4.5 ml. of benzene. Upon addition of the bromine-benzene solution slowly with stirring, the nickel solution turned green. After one hour the resulting solution was filtered and the precipitate extracted with hexane. The product contained 1.45 (48%) of di(triethylphosphine)nickel tribromide having a melting point of 86°–87° C.

A reaction vessel was charged with 1.06 g. (2.0 mmol.) of the di(triethylphosphine)nickel tribromide, 1.0 g. (10 mmol.) of hydroxybenzene, 1.5 g. (11.6 mmol.) of diisopropylmonoethylamine, and 25 ml. of benzene. The resulting mixture was stirred and carbon monoxide was bubbled through the resulting solution. The hydroxybenzene was added after the carbon monoxide addition was initiated. The resulting solution changed color to dark green to yellow-brown. An analysis of the reaction products by gas chromotography showed no diphenylcarbonate.

In a preferred embodiment of my invention, set out in Examples XV to XIX, which follow, the Group VIIIB element is at the first oxidation level greater than zero at the beginning of the reaction. This embodiment, which is the subject matter of the J. E. Hallgren U.S. patent application, Ser. No. 731,493 filed contemporaneously herewith, has been found to provide improved results and so is disclosed also herein, although not essential to the utility of this invention.

EXAMPLE XV

Preparation of the polycarbonate of bisphenol-A by contacting bis(4-hydroxyphenyl)propane-2,2, carbon monoxide, diisopropylmonoethylamine, and poly[palladium(I)monocarbonyl chloride].

Poly[palladium(I)monocarbonyl chloride] was prepared by modification of the literature procedure of W. Schnabel and E. Koker, J. Organomet, Chem. 19, 455 (1969). The procedure involved the addition of 0.77 g. (2.0 mmol.) of bis(benzonitrile)palladium(II) dichloride to 200 ml. of chloroform. Carbon monoxide was passed through the resulting solution slowly until a yellow precipitate formed and the color of the organic phase was discharged. The mixture was filtered and the precipitate dried at room temperature in vacuo. Subsequent work-up and analysis showed the presence of 0.24 g. (72% yield) of poly[palladium(I)monocarbonyl chloride].

A 50 ml. 4-neck resin kettle fitted with a gas addition type hollow turbine stirrer, septum cap and gas outlet was charged with 5.15 g. (0.030 mol.) of poly[palladium(I)monocarbonyl chloride] of the empirical formula $[Pd(CO)Cl]_x$, 3.29 g. (0.014 mol.) of bisphenol-A and 25 ml. of methylene chloride. Carbon monoxide was bubbled through the resulting slurry and 7.84 g. (0.061 mol.) of diisopropylmonoethylamine was added. The reaction mixture turned black immediately. Passage of the carbon monoxide through the reaction media was continued for about 15 hours. The resulting reaction products were filtered, the filtrate was concentrated and precipitated by addition to 300 ml. of vigorously stirred methanol. The resulting polymer was collected by filtration, redissolved, filtered and reprecipitated. Polymer was dried overnight in vacuo at 100° C. Gel permeation chromatography (GPC) analysis of the reaction mixture showed the presence of a polycarbonate of bisphenol-A containing recurring units of the formula:

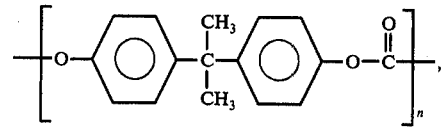

wherein $n$ is an integer averaging at least about 6. A resume of reaction conditions and products describing phenolic reactant, bisphenol-(—OH) group to palladium mole ratio, yield of polycarbonate on a weight basis, $\overline{M}_n$ number average molecular weight, $\overline{M}_w$ weight average molecular weight, $\overline{M}_w/\overline{M}_n$, $\bar{n}$ = average degree of polymerization is set out in Table I which follows:

TABLE I

| Phenolic Reactant | Mole Ratio OH:Pd | Yield (wt./%) | $\overline{M}_n$ | $\overline{M}_w$ | $\overline{M}_w/\overline{M}_n$ | $\bar{n}$ |
|---|---|---|---|---|---|---|
| BPA[1] | 1.0 | 5[2] | 1714[3] | 2053[3] | 1.20[3] | 6 |

[1]bisphenol-A
[2]% recovered by weight after precipitation of a 5% $CH_2Cl_2$ solution into methanol
[3]GPC data using polystyrene standards in $CH_2Cl_2$

EXAMPLE XVI

Preparation of a polycarbonate of bisphenol-A using a monocarbonate oligomer of bis(4-hydroxyphenyl)propane-2,2 as the phenolic reactant.

The preparations of the poly[palladium(I)monocarbonyl chloride] and the polycarbonate were conducted as set out in Example XV, except as noted hereafter. The reaction medium contained 0.076 g. (0.45 mmol.) of poly[palladium(I)monocarbonyl chloride], 0.087 g. (0.18 mol.) of bisphenol-A monocarbonate, 3 ml. of methylene chloride and 0.12 g. (0.90 mmol.) of diisopropylmonoethylamine. GPC analysis of the reaction product mixture determined the presence of a polycarbonate of bisphenol-A containing recurring units of the Example XV formula. A resume of the reaction is set out in Table II which follows:

TABLE II

| Phenolic Reactant | Mole Ratio OH:Pd | Yield (wt./%) | $\overline{M}_n$ | $\overline{M}_w$ | $\overline{M}_w/\overline{M}_n$ | $\overline{n}$ |
|---|---|---|---|---|---|---|
| BPA—C(=O)—BPA[1] | 0.8 | 50[2] | 1773[3] | 2501[3] | 1.41[3] | 6 |

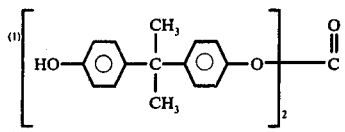

[2)(3)]as in Example XV, Table I

EXAMPLE XVII

Preparation of a polycarbonate of bisphenol-A using 2,2,6,6,N-pentamethylpiperidine as a base.

The preparations of the poly[palladium(I)monocarbonyl chloride] and the polycarbonate were conducted as set out in Example XV, except as noted hereafter. The reaction medium contained 2.669 g. (15.71 moles) of poly[palladium(I)monocarbonyl chloride], 1.345 g. (5.89 mmol.) of bisphenol-A, 15 ml. of methylene chloride and 3.659 g. (23.56 mmol.) of 2,2,6,6,N-pentamethylpiperidine. The reaction products were concentrated in 100 ml. of methanol and dried at 80° C. GPC analysis of the reaction mixture show the presence of 1.42 g. (95% yield) of a polcarbonate of bisphenol-A containing the recurring units of the Example XV formula. A resume of the reaction is set out in Table III.

TABLE III

| Phenolic Reactant | Mole Ratio OH:Pd | Yield (wt./%) | $\overline{M}_n$ | $\overline{M}_w$ | $\overline{M}_w/\overline{M}_n$ | $\overline{n}$ |
|---|---|---|---|---|---|---|
| Bisphenol-A[1] | 0.75 | 95[2] | 5000[3] | 9000[3] | 1.8[3] | 20 |

[1)(2)]as in Example XV, Table I
[3]GPC data using polycarbonate standards in tetrahydrofuran

EXAMPLE XVIII

Preparation of a polycarbonate of bisphenol-A using poly[palladium(I)monocarbonyl bromide].

The preparations of poly[palladium(I)monocarbonyl bromide] and the polycarbonate were conducted as set out in Example XV, except as noted hereafter.

The poly[palladium(I)monocarbonyl bromide] procedure involved the use of 0.77 g. (2.0 mmol.) of bisbenzonitrile palladium(II)dibromide, and resulted in a 49% yield of poly[palladium(I)monocarbonyl bromide]. The reaction medium contained 2.00 g. (9.3 moles) of poly[palladium(I)monocarbonyl bromide], 0.96 g. (4.2 mmol.) of bisphenol-A, 20 ml. of methylene chloride and 2.89 g. (18.6 mmol.) of 2,2,6,6,N-pentamethylpiperidine. The reaction products were in 100 ml. of methanol and dried at 60° C. GPC analysis showed the presence of 0.97 g. (91% yield) of a polycarbonate of bisphenol-A containing the recurring units of the Example XV formula. A resume of the reaction is set out in Table IV.

TABLE IV

| Phenolic Reactant | Mole Ratio OH:Pd | Yield (wt./%) | $\overline{M}_n$ | $\overline{M}_w$ | $\overline{M}_w/\overline{M}_n$ | $\overline{n}$ |
|---|---|---|---|---|---|---|
| Bis- | | | | | | |

TABLE IV-continued

| Phenolic Reactant | Mole Ratio OH:Pd | Yield (wt./%) | $\overline{M}_n$ | $\overline{M}_w$ | $\overline{M}_w/\overline{M}_n$ | $\overline{n}$ |
|---|---|---|---|---|---|---|
| phenol-A[1] | 0.9 | 91[2] | 8000[3] | 16,000[3] | 2.0[3] | 32 |

[1)(2)]as in Example XV, Table I
[3]as in Example XVII, Table III

EXAMPLE XIX

Preparation of a polycarbonate of bisphenol-A using the polycarbonate product of Example XVIII as the phenolic reactant.

The preparations of the poly[palladium(I)monocarbonyl chloride] and the polycarbonate was conducted as set out in Example XV except as noted hereafter. The reaction medium contained 0.086 grams, (0.40 mmol.) of poly[palladium(I)monocarbonyl chloride], 0.500 grams of the polycarbonate product of Example XVIII, 16 ml. of methylene chloride and 0.124 g. (0.80 mmol.) of 2,2,6,6,N-pentamethylpiperidine. The reaction products were concentrated in 100 ml. of methanol and dried at 80° C. GPC analysis showed the presence of 0.43 g. (86% yield) of a polycarbonate of bisphenol-A containing the recurring units of the Example XV formula. A resume of the reaction is set out in Table V:

TABLE V

| Phenolic Reactant | Mole Ratio OH:Pd | Yield (wt./%) | $\overline{M}_n$ | $\overline{M}_w$ | $\overline{M}_w/\overline{M}_n$ | $\overline{n}$ |
|---|---|---|---|---|---|---|
| Bisphenol-A[1] | n.d. | 86[2] | 11,000[3] | n.d. | n.d. | 44 |

[1]polycarbonate of bisphenol-A of Example XVIII
[2)(3)]as in Example XV, Table I
n.d. - not determined As illustrated by the preparation of polycarbonates of bisphenol-A in Examples XVI to XIX above, in general the aromatic polycarbonates that can be prepared by my process are oligomeric or polymeric and have an intrinsic viscosity range of as high as 1.5 or even higher deciliters per gram (dl./g.) as measured in methylene chloride. Especially useful are polycarbonate resins which are generally suited to the preparation of films, sheets, fibers, laminates or reinforced plastics (e.g. for insulating or protective coating applications) by conventional techniques which have an intrinsic viscosity of from about 0.35 to about 0.7 dl./g.

EXAMPLE XX

Preparation of diphenyl carbonate using iridium(I)-tricarbonyl chloride.

A reaction vessel was charged with 0.31 g. (1.0 mmol.) of iridum(I)tricarbonyl chloride, i.e. Ir(CO)$_3$Cl, commercially available from "Strem Chemicals, Inc.", 0.19 g. (2.0 mmol.) of hydroxybenzene and 7 ml. of chlorobenzene. Carbon monoxide was bubbled through the mixture and 0.26 g. (2.0 mmol.) of diisopropylmonoethylamine was added. Subsequent work-up and analysis showed the presence of 0.021 g. (10% yield) of diphenyl carbonate.

EXAMPLE XXI

Preparation of diphenylcarbonate using rhodium(III) trichloride.

A reaction vessel was charged with 4 g. (42.0 mmol.) of hydroxybenzene and 0.83 g. (4.0 mmol.) of rhodium trichloride, i.e. $RhCl_3$. The mixture was warmed to 100° C., carbon monoxide was bubbled through the mixture and 2.5 g. (16.0 mmol.) of 2,2,6,6N-pentamethylpiperidine was added. Subsequent workup and analysis showed the presence of diphenylcarbonate (estimated yield 1%) and 0.7 g. (8%) of phenyl salicylate.

EXAMPLE XXII

Preparation of diphenylcarbonate using bis(tetrapropylammonium)dicarbonyl tetrachloroplatinite(I).

The bis(tetrapropylammonium)dicarbonyl tetrachloropaltinite(I) was prepared by the procedure of Goggin and Goodfellow, J. Chem. Soc. (Dalton) (1973) 2355. The reaction vessel was charged with 0.48 g. (0.5 mmol.) of bis(tetrapropylammonium)dicarbonyl tetrachloroplatinite(I), 0.38 g. (4.0 mmol.) of phenol, and 7 ml. of methylene chloride. Carbon monoxide was bubbled through the mixture and 0.62 g. (4.0 mmol.) of 2,2,6,6,N-pentamethylpiperidine was added. Subsequent work and analysis showed the presence of diphenylcarbonate estimated at a 2% yield.

In the practice of my process, the Group VIIIB elements — after separation from the resulting aromatic carbonate product — can be oxidized by any means to an oxidation state greate than zero, and can be reemployed, that is recycled, in the aromatic process described herein. In my copending application Serial No. (Docket RD-9366) filed concurrently herewith, procedures by which Group VIIIB elements can be oxidized are described in detail and the description of these procedures is incorporated herein in this specification in their entirety by reference.

Although the above examples have illustrated various modifications and changes that can be made in carrying out my process, it will be apparent to those skilled in the art that other Group VIIIB metals, phenol compounds, ligands, bases and solvents, etc., can be used in the particular embodiments of the invention described which are within the full intended scope of the invention as defined by the appended claims.

I claim:

1. An aromatic carbonate process which comprises contacting a phenol with carbon monoxide, a base, and a Group VIIIB element selcted from ruthenium, rhodium, palladium, osmium, iridium or platinum having an oxidation state greater than zero.

2. The claim 1 process, wherein said element is present in an ionic form.

3. The claim 1 process, wherein said element oxidation state is at least +2.

4. The claim 1 process, wherein said base is a sterically hindered amine.

5. The claim 1 process, wherein said element is associated with a carbonyl group.

6. The claim 1 process, wherein said element is associated with a halide.

7. The claim 1 process, wherein said element is coordinated with a ligand selected from an arsine, a stibine, a phosphine, a nitrile or a halide.

8. The claim 1 process, wherein said element is associated with an inorganic halide compound.

9. The claim 1 process, wherein methylene chloride is employed as a solvent, the base is diisopropylmonoethylamine, the phenol is 4-methylphenol, the Group VIIIB element is palladium in the form of palladium(II) dichloride.

10. The claim 1 process in which diphenyl carbonate is prepared in a methylene chloride solution in which the base is diisopropylmonoethylamine, the phenol is phenol, and the Group VIIIB element is palladium in the form of bis(benzonitrile) palldium(II) dichloride.

11. The claim 1 process, further comprising, after the preparation of the aromatic carbonate, separating at least a portion of any resulting Group VIIIB element or compound from said carbonate, oxidizing at least a portion of said resulting Group VIIIB element or compound to an oxidation state greater than zero, and recycling at least a portion of said oxidized element in said aromatic carbonate process.

12. An aromatic polycarbonate process which comprises contacting an aromatic polyphenol with carbon monoxide in the presence of a base and a Group VIIIB metal selected from the class consisting of ruthenium, rhodium, palladium, osmium, iridium and platinum having an oxidation state greater than zero.

13. An aromatic polycarbonate process which comprises contacting an aromatic bisphenol of the formula:

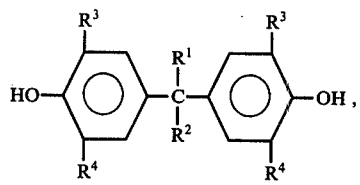

where independently each $R^1$ and $R^2$ is hydrogen, $C_{1-4}$ alkyl or phenyl and independently each $R^3$ and $R^4$ is hydrogen or $C_{1-4}$ alkyl, with carbon monoxide in the presence of a base and a Group VIIIB metal selected from the class consisting of ruthenium, rhodium, palladium, osmium, iridium and platinum having an oxidation state greater than zero.

14. The claim 13 process, wherein $R^1$ and $R^2$ are methyl and at least one of $R^3$ and $R^4$ is hydrogen.

15. The claim 14 process, wherein the base is a tertiary amine.

16. The claim 15 process, carried out in the presence of an inert solvent.

17. An aromatic polycarbonate process which comprises contacting an aromatic bisphenol of the formula:

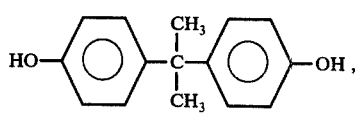

with carbon monoxide in the presence of a base and a Group VIIIB metal selected from the class consisting of ruthenium, rhodium, palladium, osmium, iridium and platinum having an oxidation state greater than zero.

18. An aromatic monocarbonate process which comprises contacting an aromatic phenol of the formula:

wherein $R_a$ represents an aromatic radical wherein the —OH radical is attached directly to an aromatic ring carbon atom and $x$ is the number 1, with carbon monoxide, a base, and a Group VIIIB element selected from the class consisting of ruthenium, rhodium, palladium, osmium, iridium and platinum having an oxidation state greater than zero.

19. The claim 18 process, wherein $R_a$ is selected from carbo- or heteromonocyclic, polycyclic or fused polycyclic radicals.

20. The claim 19 process, wherein the base is a tertiary amine.

21. The claim 20 process, carried out in the presence of an inert solvent.

22. An aromatic monocarbonate process which comprises contacting a phenol of the formula:

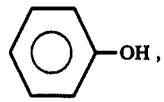

with carbon monoxide, a base, and a Group VIIIB element selected from the class consisting of ruthenium, rhodium, palladium, osmium, iridium and platinum having an oxidation state greater than zero.

* * * * *